(12) United States Patent
Naghieh et al.

(10) Patent No.: US 6,754,414 B2
(45) Date of Patent: Jun. 22, 2004

(54) IMAGING OF MICROARRAYS USING FIBER OPTIC EXCITER

(75) Inventors: Harry R. Naghieh, Hayward, CA (US); James W. Hillendahl, Vacaville, CA (US); David E. Waldbeser, Martinez, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 51 days.

(21) Appl. No.: 10/252,022

(22) Filed: Sep. 19, 2002

(65) Prior Publication Data

US 2003/0128910 A1 Jul. 10, 2003

Related U.S. Application Data

(60) Provisional application No. 60/325,855, filed on Sep. 27, 2001, and provisional application No. 60/325,968, filed on Sep. 27, 2001.

(51) Int. Cl.$^7$ .............................. G02B 6/00; G02B 6/36
(52) U.S. Cl. ........................... 385/33; 436/43; 359/127
(58) Field of Search .............................. 385/24, 33, 37, 385/1, 47; 359/127, 130, 391, 393, 394; 422/60, 100; 436/43, 164

(56) References Cited

U.S. PATENT DOCUMENTS

| 4,278,327 A | | 7/1981 | McMahon et al. |
|---|---|---|---|
| 5,232,068 A | | 8/1993 | Linsley et al. |
| 5,578,818 A | | 11/1996 | Kain et al. |
| 6,215,560 B1 | * | 4/2001 | Yguerabide et al. ......... 435/7.1 |
| 6,362,004 B1 | | 3/2002 | Noblett |
| 6,407,858 B1 | | 6/2002 | Montagu |
| 6,512,618 B1 | | 1/2003 | Heflinger |
| 2003/0032039 A1 | * | 2/2003 | Cunningham et al. ......... 435/6 |
| 2003/0059855 A1 | * | 3/2003 | Cunningham et al. ....... 435/7.9 |
| 2003/0148391 A1 | * | 8/2003 | Salafsky ..................... 435/7.2 |

FOREIGN PATENT DOCUMENTS

WO    WO 00/62549 A1    10/2000

OTHER PUBLICATIONS

Jing, W. "NA of the single mode fiber," at <<http://laser.physics.sunysb.edu/~wjing/presentation / >> visited on Jul. 24, 2002, 7 pages total.

La Rosa, A.H. et al. "Optical imaging of carrier dynamics in silicon with subwavelength resoultion," *Appl. Phys. Lett.* Mar. 1997, pp. 1656–1658, vol. 70, No. 13.

* cited by examiner

*Primary Examiner*—Akm Enayet Ullah
(74) *Attorney, Agent, or Firm*—M. Henry Heines; Townsend and Townsend and Crew LLP

(57) ABSTRACT

Microarrays are imaged by an illumination and detection system that supplies excitation light through one or more optical fibers, each fiber transmitting excitation light from an excitation light source to a single spot in the microarray. Emission light from each spot is then collected by a collimating lens and converted to a signal that is compiled by conventional software into an image of the entire microarray. The optical fiber(s) and the collimating lens are arranged such that the direction of travel of the excitation light and the direction along which the emission light is collected are not coaxial, and preferably both are at an acute angle to the axis normal to the plane of the microarray.

17 Claims, 2 Drawing Sheets

IMAGING OF MICROARRAYS USING FIBER OPTIC EXCITER

CROSS REFERENCE TO RELATED APPLICATION

This application claims the benefits of co-pending U.S. provisional patent applications Nos. 60/325,855 and 60/325,968, both filed on Sep. 27, 2001, for all purposes legally capable of being served thereby. The contents of each of these provisional patent applications are incorporated herein by reference in their entirety, as are all other patent and literature references cited throughout this specification.

BACKGROUND OF THE INVENTION

1. Field of the Invention

This invention resides in the field of imaging of microarrays by optical excitation of materials in the arrays and detection of the emissions resulting from the excitation, and particularly in systems for conveying excitation light to microarrays.

2. Description of the Prior Art

Numerous devices are commercially available for reading DNA microarrays as well as microarrays of other materials. Examples of these devices are the Chip Scanner technologies of Affymetrix, Inc., Santa Clara, Calif., USA, confocal laser scanners of Agilent Technologies, Palo Alto, Calif., USA, the GenePix microarray scanners of Axon Instruments, Inc., Union City, Calif., USA, the DNAscope™ confocal scanners of GeneFocus, Waterloo, Ontario, Canada, the GeneTAC™ microarray analyzers of Genomic Solutions, Inc., Ann Arbor, Mich., USA, the ScanArray™ Microarray Analysis Systems of Packard BioScience Company, Meriden, Conn., USA, and laser scanning systems of Virtek Vision Corporation, Waterloo, Ontario, Canada.

These devices utilize a lens and mirror system that focuses excitation light from one or more lasers onto individual spots in an array of spots. The emission light from each spot is collected by a lens system with optical bandpass emission filters and one or more photomultiplier tube (PMT) detectors. An image of the array is formed by scanning the narrow excitation source beam and the emission collection optics over the sample. This is achieved by moving either the optics or the sample. This mechanism suffers limitations in sensitivity and in the level of detection and resolution of the resulting image. Systems with a common laser path generally suffer from dichroic optical filter efficiency problems, since rejection of the very strong excitation light is accompanied by rejection of a substantial portion of the much weaker emission light. Further inefficiencies arise from the laser scanning systems in these devices which use confocal pinholes to remove undesirable background, including crosstalk from neighboring array spots, since this reduces the signal light as well.

Devices are also available that deliver broadband white light onto a large area of the sample, and utilize a lens system with optical bandpass emission filters and a CCD detector to collect and quantify the emission light. In one such device, which is available from Applied Precision, Inc. of Issaquah, Wash., USA, and is described in International Patent Publication No. WO 00/62549, international publication date Oct. 19, 2000, a small area (a few square millimeters) is illuminated by a fiber optic ring illuminator. The illuminator is a multiple optical fiber bundle with a working distance ranging from several tenths of an inch to several inches to flood a large number of microarray spots with uniform illumination. Images are formed in panels, each containing all of the microarray spots that were simultaneously illuminated by the fiber bundle. Different image panels representing different portions of the sample are obtained by moving the sample relative to the optical system, and a sufficient number of image panels are collected in this manner to encompass the entire sample. Adjacent panels are then joined or "stitched" together to form a complete image of the sample. Formation of the complete image in this manner requires an expensive precision motion stage, and the stitching is a complicated and laborious process, limiting the quality of the data that this device can generate. A similar device, available from Alpha Innotech Corporation of San Leandro, Calif., USA, floods the entire sample with light and uses a CCD camera to obtain an image of the entire microarray. Current commercially available CCD detectors are of limited resolution, however. In both the Applied Precision and Alpha Innotech devices, crosstalk occurs between array spots.

SUMMARY OF THE INVENTION

The present invention resides in illumination and detection systems for microarrays, the systems supplying excitation light through one or more optical fibers, each transmitting excitation light from one or more excitation light sources to a single spot in the array. Emission light generated by each spot is collected, preferably without the use of an optical fiber, by a collimating lens and converted by a detector to a signal that can be processed by conventional imaging software. The collimating lens is preferably used in conjunction with an optical filter. Further signals are obtained by rastering either the microarray or the optical system, and the various signals are compiled by imaging software to form an image of the entire microarray. This system is applicable to any microarrays that utilize labels that emit a signal upon optical excitation. Preferred labels are fluorophores and fluorescent emissions, but the invention extends as well to phosphors and other types of optically excitable labels known to those familiar with biochemical assays.

The optical system is arranged such that the direction of travel of the excitation light differs from the direction along which the emission light is collected, i.e., the two paths do not have a common axis. The optical fiber is configured to illuminate the spot directly, preferably at an acute angle relative to the axis normal to the microarray. The angle of incidence of the excitation light is preferably an acute angle as well. The illumination fiber is configured such that the beam emerging from the fiber is either non-diverging or only minimally diverging.

Preferred light sources are those supplying ultraviolet, visible, or near-infrared light, optically coupled with the optical fiber so that substantially all of the light from the light source enters the fiber for transmission to the spot to be illuminated. The result is substantially no loss of intensity between the light source and the spot. The optical fiber may be a simple fiber or one that includes a collimator, an optical filter, or a collimator-filter-collimator assembly, or any other optical elements or components that process the light in various ways that will enhance its use for particular applications and assays. The output tip of the fiber is preferably shaped to reduce the divergence of the emerging light beam.

Systems in accordance with this invention offer numerous advantages over the prior art. By illuminating only the test area of interest, these systems eliminate crosstalk and maximize the signal of interest. Furthermore, by separating the excitation and emission light paths, systems in accordance with this invention limit the excitation and emission optics to a single function each, thereby permitting individual optimization of these two optical systems. This leads to maximal signal collection and superior performance for any given level of detection and sensitivity. In systems in which the illumination fiber and the emission collection optics are at different angles relative to the normal axis, very little of the excitation light is detected in the emission light path, and a maximal signal-to-noise ratio is achieved. Systems in accordance with this invention thus provide a means of directing excitation light to each individual spot of a microarray in a highly efficient manner while minimizing crosstalk and optimizing the collection of emission light with the highest sensitivity and resolution. Furthermore, excitation systems of this invention require no additional lenses or other optical elements between the excitation fiber and the microarray, and can thus avoid the losses in light intensity that are often caused by these additional elements. In aspects of this invention that are directed to an optical fiber optically coupled directly to an LED or SLD light source, the coupled product is inexpensive, durable, and compact, and delivers bright light while generating minimal heat. This simplified yet highly efficient design presents advantages for packaging, cost and size reduction.

DETAILED DESCRIPTION OF THE INVENTION AND PREFERRED EMBODIMENTS

Figure 1:
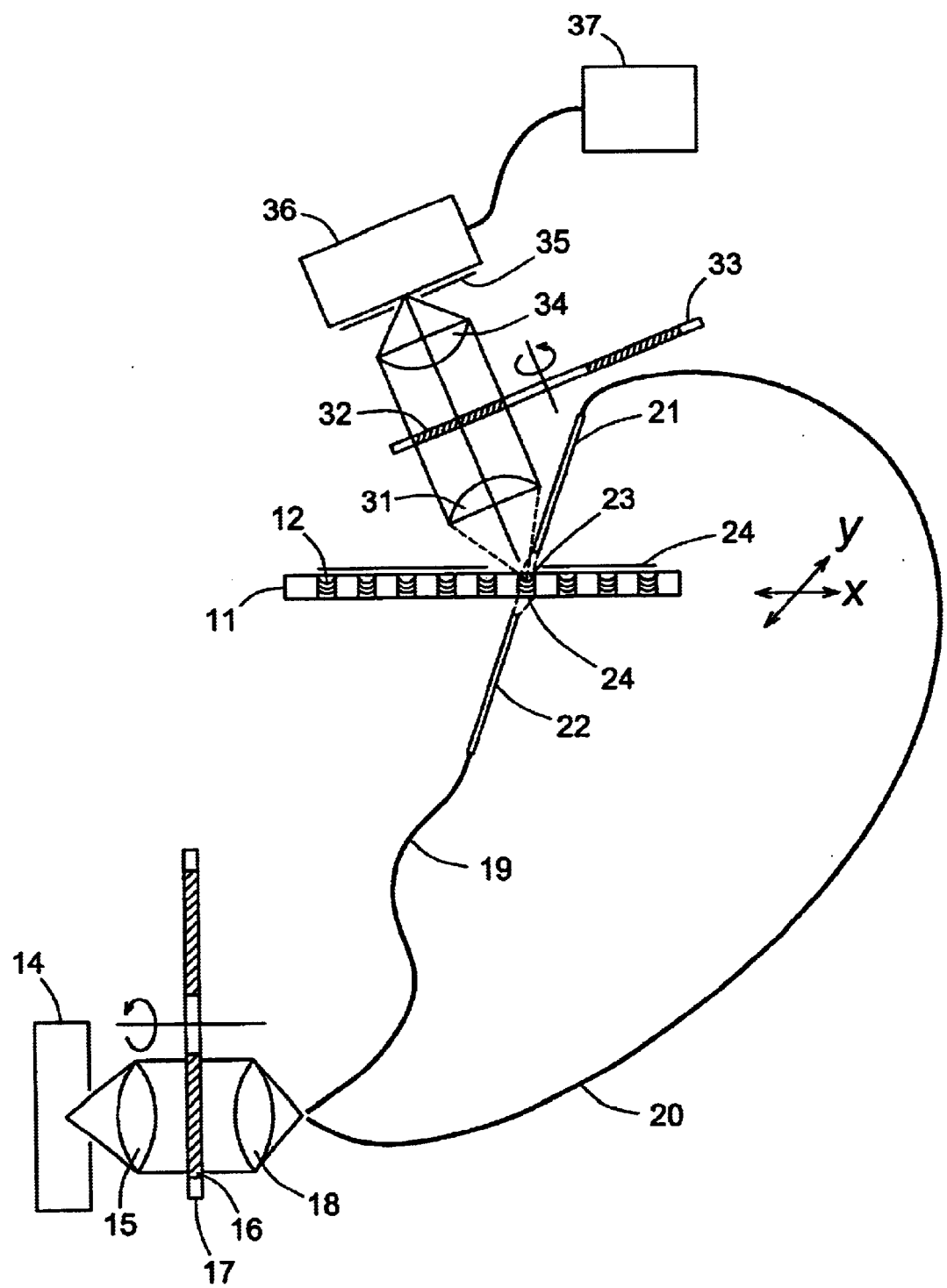
FIG. 1 is a diagram of an imaging system for microdot arrays utilizing the features of the present invention.

Microarrays are generally planar arrays, typically two-dimensional rectangular arrays, of microdots, referred to herein as "spots," each spot measuring at most 500 microns in diameter and containing a test specimen to be analyzed by chemical or biochemical assays for either diagnostic or screening purposes. The most common such specimens are nucleic acid segments, although biological species of various kinds have been used and can be used here as well. The spots in a microarray are processed in parallel in accordance with the analyses, the spots containing labels such as fluorophores to indicate the successful specimens. Microarrays of this type are typically deposited on a flat, inert, and often light-transmissive substrate such as a microscope slide. Other microscopic arrays include bio-chip ("lab-on-a-chip") technologies and electrophoresis sequencing readers that include microscale and/or nano-scale fluidic channels. Examples of microarray devices of this type are those available from Aclara BioScience, Inc. (Santa Clara, Calif., USA), Nanogen, Inc. (San Diego, Calif., USA), and Caliper Technologies Corp. (Mountain View, Calif., USA).

The excitation system of this invention may contain any of a variety of different types of light sources. Examples are broadband light sources such as xenon flash lamps, quartz halogen lamps, light-emitting diodes (LEDs), vertical cavity surface-emitting lasers (VCSELs), superluminescent diodes (SLDs), and one or more simultaneous sources such as single or multiple discrete wavelength lasers. The light source is preferably optically coupled to the optical fiber. For point sources of light or sources that are nearly point sources, such as solid state sources, optical coupling may be achieved by proximity coupling. Otherwise, a coupling lens or lens system that will transmit substantially all of the light from the light source to the fiber can be used. The system can also include an optical excitation filter, a monochromator, or a tunable acousto-optic filter. The optical fiber transmits light from the light source to the sample to excite either a single label or multiple labels that are present in the sample. Emission light resulting from the excitation is collected by a collimating lens system which directs the light through an optical emission filter and then to a detector, after first optionally passing through a monochromator or a tunable acousto-optic filter. Examples of suitable detectors are photomultiplier tubes, microchannel plates, silicon PIN diodes, avalanche photodiodes (APDs), CCD detectors, and CMOS detectors.

The optical fiber is either straight or tapered along its length. The choice of fiber may vary with the particular type of array to be imaged. A single-mode fiber with cladding and outer buffer coating is preferred, particularly one with a mode field diameter (MFD) small enough to produce an illumination beam appropriate for a single spot. A preferred mode field diameter range is 3 to 5 microns. An example of a clad single mode optical fiber is 3M Company part no. FS-SN-3224, 3M Company, St. Paul, Minn., USA, with MFD/cladding/buffer dimensions of 4/125/250 microns, and a numerical aperture (the sine of the divergence angle $\theta$) of 0.12.

The optical fiber can have either a standard tip or a specialized tip on either or both of its ends, or a combination of both. Specialized tips that are particularly useful on the delivery end of the fiber include tips that have been shaped by melting or cutting to control the shape of the emerging beam, as well as tips to which a light-directing component such as a ball lens has been affixed or integrated by fritting, gluing or other methods. Optical fibers with shaped or integrated tips as described in this paragraph are available from Polymicro Technologies referenced above. The delivery tip of the optical fiber is preferably placed very close to the spot, preferably within about 0.1 mm to about 3 mm of the spot, and most preferably within about 0.1 mm to about 1 mm.

The angle of incidence of the excitation light traveling from the optical fiber to an individual spot on the microarray and the direction of the path along which the emission light is detected are both measured relative to the axis normal to the microarray. In preferred embodiments, these angles are each within the range of about 5° to about 60°, and preferably from about 10° to about 45°. The excitation light emerging from the fiber and the emission collection path are preferably arranged symmetrically about the axis, together forming an angle within the range of about 40° to about 50°, i.e., the angle formed by combining the angle of the fiber relative to the axis normal to the array with the angle of the emission path relative to the same axis. A particularly preferred combined angle is 45°.

Of the various types of light sources that can be used in the practice of this invention, broadband LEDs are preferred. This and other types of light source can also include a phosphor or other broadband conversion element upstream of the coupling to the fiber. The conversion element can be a coating on the light source, or it can be incorporated in the plastic packaging of the light source or in a gel or other discrete closed package. As a further alternative, the conversion element can be intagliated into the end of the fiber itself.

The optical coupling between the light source and the optical fiber can be achieved by a focusing lens or lens system located between the light source and the optical fiber, or by direct coupling of the optical fiber to the light source. Examples of focusing lens systems are a ball lens, a pair of microscope objectives, and a condenser pair of plano convex lenses. Proximity coupling, i.e., direct coupling of the fiber to the light source, is preferred. LEDs and SLDs, which are readily available from commercial suppliers, can be readily modified by removing the lens system supplied by the manufacturer and placing the flat fiber end very close to, and preferably in direct secured contact with, the glowing LED or SLD itself. An optically clear cement with low autofluorescence can be used. Examples of such a cement are Norland Optical Cement NOA 73 and NOA 61, Norland Products, Inc., Cranbury, N.J., USA. Alternatives to cements are gels or oils that are optically clear. To stabilize the coupling, the LED or SLD and the fiber end can be encased in a metal tube, a straight tip (ST) connector, or any other packaging, with one end of the connector joined to the LED or SLD and the other to the optical fiber.

While the novelty-defining concepts and features of the invention can be implemented in many different configurations and arrangements, a convenient way to achieve an understanding of these features is to study individual systems within the scope of the invention. Such a system is depicted in the Figures.

The system shown in FIG. 1 is arranged for the imaging of a microarray 11 whose spots 12 may contain any of a variety of materials including, but not limited to, nucleic acids, oligonucleotides, polynucleotides, non-nucleic acid organic or inorganic chemical species, oligomers, polymers, and proteins. The microarray 11 can also be a non-positional array or "lab-on-a-chip" system. The species in each spot has been treated with any of various labels, notably fluorochrome dyes or probes, and the microarray is supported by a glass plate, nylon film, or other equivalent support. The spot size is not critical and can vary, although in most cases the spot size will be 500 microns in diameter or less, preferably from 5 to 500 microns in diameter. The microarray 11 is held by a holding fixture 13 which moves or rasters the microarray in the x and y directions within a plane that is transverse to the direction of the optical paths through which excitation and emission collection are performed. This rastering movement enables the system to capture signals sequentially from the entire microarray. Alternatively, the microarray can be held stationary and the optics made movable in the x and y directions across the microarray surface.

An excitation light source 14, which may be a broadband source such as for example a xenon lamp, a quartz halogen lamp, an LED, an SLD, or a narrow band source such as for example a single or multiple discrete wavelength laser, illuminates a collimating lens 15. Alternatively, two or more discrete lasers can be used simultaneously with a single fiber. The collimated light emerging from the collimating lens 15 passes through an optical excitation filter 16 on a multi-position filter wheel 17. The filter wheel permits the selection of particular excitation wavelengths from a variety of wavelengths, and the rotation and position of the wheel can be controlled by software appropriately adapted to particular experimental protocols. As alternatives to the optical excitation filter, a monochromator or a tunable acousto-optic filter may be used. A second lens 18 focuses the light and couples it into an optical fiber 20. The fiber terminates in a fiber holder 21 whose output or delivery end is positioned in close proximity to a spot 12 on the microarray 11.

In the system shown in FIG. 1, no additional lenses or optics are located between the fiber holder 21 and the microarray 11. As noted above, the fiber holder may have a shaped fiber tip such as an integrated ball lens or other type of integrated lens to lessen the divergence of the emerging beam or eliminate the divergence entirely. One example of a divergence angle is 6.9 degrees, but greater or lesser angles can be used as well. In terms of the numerical aperture, a preferred range for the numerical aperture is from about 0.10 to about 0.30, and a presently preferred numerical aperture is 0.12 (corresponding to a divergence angle of 6.9 degrees). Fibers and fiber holders with shaped tips for these and other purposes are available from Polymicro Technologies, Inc., Phoenix, Ariz., USA, and other suppliers.

Returning to FIG. 1, light emerging from the fiber tip illuminates only the single spot to which the fiber is directed, or a portion of the spot. The fiber tip is close enough to the spot to cause little, if any, excitation light to reach neighboring spots, and crosstalk is consequently eliminated or reduced to insignificant levels. Optionally, a mask 23 can be positioned above the microarray to further assure that the spot of interest does not receive any stray excitation or to protect the microarray from dust or other array contaminants.

The emission light that the spot 12 emits upon excitation is collected by a collimating lens 31, and the collimated emission light passes through an optical emission filter 32 on a multi-position filter wheel 33. Alternatively, a monochromator or tunable acousto-optic filter can be used in place of the optical emission filter 32. A second lens 34 then focuses the collimated light through an aperture 35 to control stray light, and light emerging from the aperture is received by a light detector 36. Examples of suitable light detectors are photomultiplier tubes, silicon PIN diodes, avalanche photodiodes (APDs), CCD detectors, and CMOS detectors. The detector 36 registers the emission light intensity and sends an output signal to processing and control electronics 37 and then to a computer 38 which compiles the signals from the various spots into an image of the entire microarray. With the fiber holder 21 at an angle relative to the axis normal to the plane of the microarray, very little excitation light will enter the emission light path.

These systems and other systems within the scope of this invention are readily adaptable to achieve signal generation and processing by Time-Resolved Fluorescence. This is accomplished for example by using a flashlamp, an LED, or an SLD as the light source, imposing a controlled delay time between a flash of the light source and the signal collection, and allowing for programmable variable signal collection integration time. The only modifications needed to achieve this are modifications of the software and electronics, and such modifications will be readily apparent to those skilled in the art of Time-Resolved Fluorescence.

In further embodiments of the invention, the system includes a multitude of optical excitation fibers arranged either in a linear array or an x-y (two-dimensional) array rather than a single fiber. Each individual excitation fiber is associated with a separate collection channel, and the entire fiber array can be moved across the microarray, or the microarray moved relative to the fiber array, and in either case signals are obtained from all spots of the microarray in a shorter span of time than would be required if only a single fiber were used.

Figure 2:
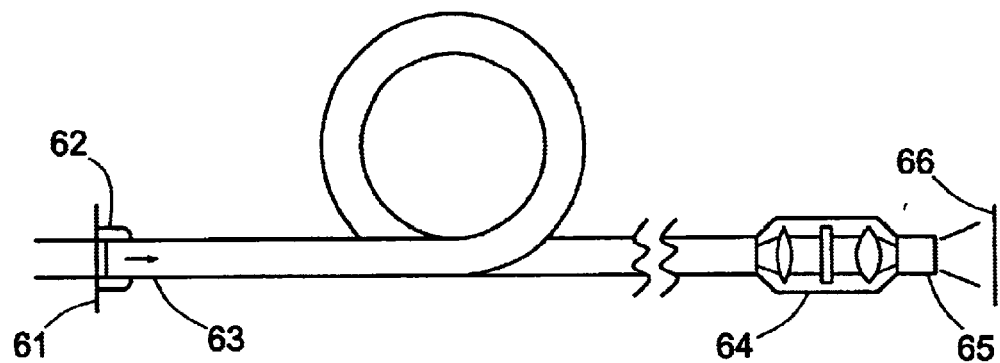
FIG. 2 is a diagram of an illumination system for use in the imaging system of FIG. 1, using an LED or SLD light source optically coupled to the fiber and an optical filter on the output end of the fiber.
Figure 3:
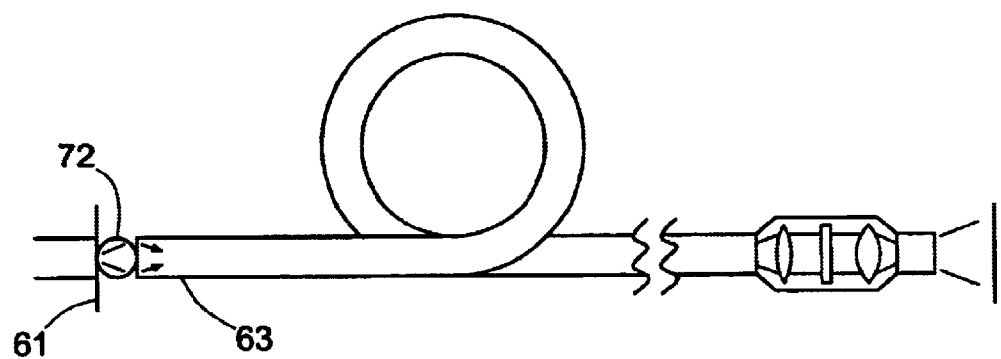
FIG. 3 is a diagram of a second illumination system which is a variation of the illumination system of FIG. 2, also for use in the imaging system of FIG. 1.

Examples of LED or SLD illumination systems in which the light source is optically coupled to the optical fiber are shown in FIGS. 2 and 3. The system of FIG. 2 includes a white light LED or SLD source 61 directly coupled to the flat end of an optical fiber 63 through an optical cement such as those described above. The coupling is surrounded by an epoxy potting compound 62 or a ring or tube. Light emerging from the LED or SLD is efficiently collected by the optical fiber 63 and transmitted to a fiber-optic device 64, which consists of a first fiber collimator for the light emerging from the LED or SLD, an optical bandpass filter, and a second fiber collimator for the light emerging from the optical bandpass filter. The filter can either be a single optical bandpass filter or multiple filters mounted on a wheel or slide, allowing the user, either manually or by automated means, to select a particular filter and thereby excite a specific fluorophore. The light emerging from the second fiber collimator returns to the fiber for delivery from the fiber tip 65 to a spot 66 on a microarray. The system of FIG. 3 has the same components as the system of FIG. 2 except that the sealant and packaging 62 of FIG. 2 are replaced by a compact lens or lens system 72.

The foregoing descriptions are offered primarily for purposes of illustration. Further modifications, variations and substitutions that still fall within the spirit and scope of the invention will be readily apparent to those skilled in the art.

What is claimed is:

1. Apparatus for imaging a microarray, said apparatus comprising:
   (a) support means for holding said microarray;
   (b) an optical system comprising:
      (i) an excitation light source,
      (ii) an optical fiber arranged to transmit excitation light from said excitation light source to a single spot of said microarray when said carrier is held by said support means, and
      (iii) a collimating lens arranged to collect emission light from said test region along an emission collection path that is not coaxial with said optical fiber;
   (c) rastering means for rastering one of said optical system and said support means relative to the other until excitation light has been transmitted to all spots of said microarray when said carrier is held by said support means;
   (d) detection means for receiving emission light collected by said collimating lens and for generating a signal from each spot representative of emission light emitted by said spot; and
   (e) imaging means for compiling signals from all of said spots and thereby forming an image of said microarray.

2. Apparatus in accordance with claim 1 in which said microarray defines an axis normal to said microarray, and said optical fiber is arranged to direct said excitation light to said spot at a first acute angle to said axis, and said emission collection path is at a second acute angle to said axis.

3. Apparatus in accordance with claim 2 in which said first and second acute angles are each from about 5° to about 60°.

4. Apparatus in accordance with claim 2 in which said first and second acute angles are each from about 10° to about 45°.

5. Apparatus in accordance with claim 2 in which said first and second acute angles form a combined angle of from about 40° to about 50°.

6. Apparatus in accordance with claim 1 in which said optical fiber has a numerical aperture of from about 0.10 to about 0.30.

7. Apparatus in accordance with claim 1 in which said optical system is stationary and said rastering means moves said support means relative to said excitation system.

8. Apparatus in accordance with claim 1 in which said support means is stationary and said rastering means moves said optical system relative to said support means.

9. Apparatus in accordance with claim 1 in which said optical system comprises a plurality of optical fibers, each optical fiber arranged to transmit light from said excitation light source to one of a plurality of spots in said microarray.

10. Apparatus in accordance with claim 1 in which said excitation light source is a UV, visible, or near-IR light source and is optically coupled to said optical fiber.

11. Apparatus in accordance with claim 10 in which said excitation light source is a member selected from the group consisting of a light-emitting diode and a superluminescent diode, and said optical fiber contacts said diode directly or through a member selected from the group consisting of an optically clear adhesive, gel, or oil.

12. Apparatus in accordance with claim 10 in which said excitation light source is a member selected from the group consisting of a light-emitting diode and a superluminescent diode, and is optically coupled to said optical fiber through a lens system directing light from said diode into said optical fiber.

13. A method for imaging a microarray, said method comprising:
   (a) transmitting excitation light from an excitation light source through an optical fiber to a single spot on said microarray;
   (b) collecting emission light from said spot by a collimating lens arranged to collect said emission light along a path not intersecting said optical fiber;
   (c) detecting emission light collected by said collimating lens and generating a signal from each spot representative of emission light emitted by said spot;
   (d) rastering either said microarray relative to said optical fiber and said collimating lens or said optical fiber and said collimating lens relative to said microarray until excitation light has been transmitted to, and emission light has been collected from, all spots of said microarray; and
   (e) compiling signals representative of emission light from all of said spots, thereby forming an image of said microarray.

14. A method in accordance with claim 13 in which step (b) comprises collecting said emission light along an emission collection path, and said optical fiber and said emission collection path form an angle of from about 40° to about 50° with each other and are arranged symmetrically about an axis normal to said array.

15. A method in accordance with claim 13 in which said optical fiber has a numerical aperture of from about 0.10 to about 0.30.

16. A method in accordance with claim 13 in which step (d) comprises rastering said microarray relative to said optical fiber and said collimating lens.

17. A method in accordance with claim 13 in which step (d) comprises rastering said optical fiber and said collimating lens relative to said microarray.

* * * * *